United States Patent [19]
Chatellier et al.

[11] Patent Number: 5,922,957
[45] Date of Patent: Jul. 13, 1999

[54] NON-DESTRUCTIVE PROCESS FOR ESTIMATING THE AGEING OF AN ARTICLE MADE OF A COMPOSITE MATERIAL

[75] Inventors: Jean-Yves François Roger Chatellier, Arcueil; Jean-Louis Fachinetti, Bondoufle, both of France

[73] Assignee: Societe Nationale d'Etude et de Construction de Moteurs d'Aviation "Snecma", Paris, France

[21] Appl. No.: 09/000,976

[22] Filed: Dec. 30, 1997

[30] Foreign Application Priority Data

Jan. 9, 1997 [FR] France .................................. 97 00136

[51] Int. Cl.⁶ .................................................. G01N 29/00
[52] U.S. Cl. ............................................................ 73/580
[58] Field of Search ............................... 73/579, 580, 599

[56] References Cited

U.S. PATENT DOCUMENTS

| | | | |
|---|---|---|---|
| 4,050,530 | 9/1977 | Storace | 73/580 |
| 4,612,807 | 9/1986 | Wunderer | 73/580 |
| 5,092,176 | 3/1992 | Buttram et al. | 73/599 |
| 5,691,474 | 11/1997 | Gerz | 73/580 |

FOREIGN PATENT DOCUMENTS

| | | |
|---|---|---|
| 0 155 630 A2 | 9/1985 | European Pat. Off. . |
| WO 92/12440 | 7/1992 | WIPO . |

*Primary Examiner*—Hezron Williams
*Assistant Examiner*—Richard A. Moller
*Attorney, Agent, or Firm*—Oblon, Spivak, McClelland, Maier & Neustadt, P.C.

[57] ABSTRACT

A non-destructive process for estimating the ageing of an article made of a composite material is described comprising a preliminary phase in which at least one chart is prepared characterizing the change in the attenuation of ultrasonic waves in the composite material as a function of weight loss thereof, and a checking phase in which the attenuation of ultrasonic waves in the article made of the composite material is measured and the weight loss of the article is determined using the chart prepared in the preliminary phase, the weight loss being representative of the ageing of the article.

4 Claims, 6 Drawing Sheets

NON-DESTRUCTIVE PROCESS FOR ESTIMATING THE AGEING OF AN ARTICLE MADE OF A COMPOSITE MATERIAL

BACKGROUND OF THE INVENTION

1. Field of the Invention

The invention relates to a non-destructive process for estimating the ageing of an article made of a composite material, and is applicable to all articles made of an organic composite material comprising a fibre-reinforced resin.

The life of an article made of an organic composite material depends upon the conditions in which it is used and, in particular, upon the thermal cycles to which it is subjected during use. Large and repetitive temperature variations applied to an organic composite material lead to a loss of material due mainly to degradation of the resin, this loss of material being accompanied by a weight loss and a loss of the mechanical properties of the composite material. In particular, the interlaminar and intralaminar shear forces increase, the breaking strength decreases and the longitudinal modulus of elasticity decreases. For safety reasons, particularly in the aviation field, an article made of a composite material must be replaced when the weight loss reaches 3% of the initial weight. It is therefore essential to be able to estimate the life of articles made of composite material and to be able to evaluate their age in terms of mechanical properties.

2. Summary of the Prior Art

At present, in order to determine the weight loss of an article made of a composite material, samples of the material are cut from the article and then chemically attacked to determine the proportions of each constituent, namely the fibres and the resin, of the composite material and to deduce from this determination the weight loss of the article. The disadvantage of this operation is that the article is destroyed by the taking of material samples and so cannot be used as often as would be desirable.

SUMMARY OF THE INVENTION

It is an object of the invention to obviate this problem and to provide a non-destructive method which makes it possible to follow the continuous change in the degradation, over time, of an article made of composite material and to determine the working life thereof, and which can be used in the actual conditions of use of the article and as often as is desirable.

For this purpose, the invention exploits the correlation which exists between the change in the weight loss of a composite material and the change in attenuation of ultrasonic waves in the composite material.

Accordingly, the invention provides a non-destructive process for estimating the ageing of an article made of a composite material, comprising a preliminary phase in which at least one chart is prepared characterising the change in the attenuation of ultrasonic waves in the composite material as a function of weight loss of the material, and a checking phase in which the attenuation of ultrasonic waves in the article made of the composite material is measured and the weight loss of the article is determined using the chart prepared in the preliminary phase.

Preferred features and advantages of the invention will become apparent from the following description of the preferred embodiments, given by way of non-limitative example, with reference to the accompanying drawings.

DETAILED DESCRIPTION OF THE INVENTION AND PREFERRED EMBODIMENTS

Figure 1:
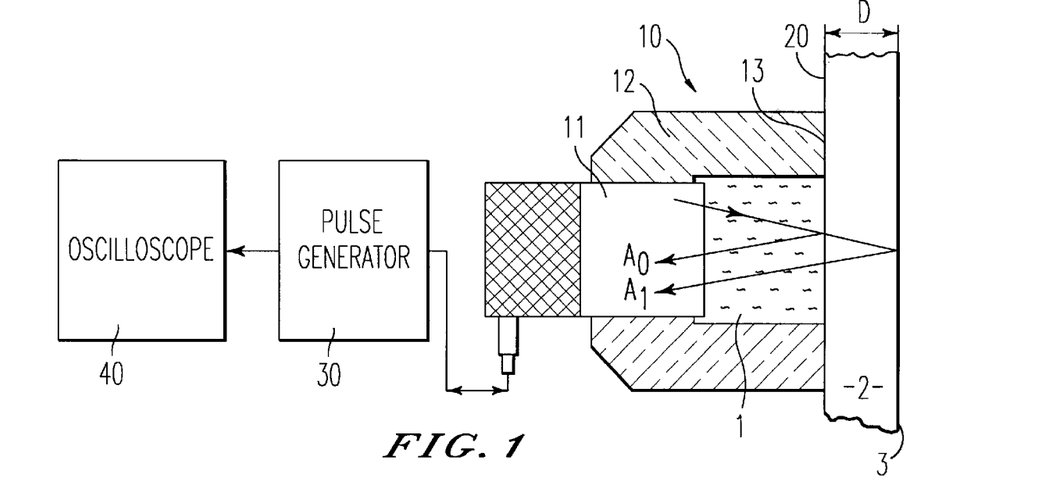
FIG. 1 illustrates diagrammatically one example of an apparatus for measuring ultrasonic wave attenuation in a composite material in a method in accordance with the invention.

The preliminary phase of the process in accordance with the invention relates to the making of a chart characterising the change, over time, of ultrasonic wave attenuation in a given composite material as a function of weight loss of the material. The chart is prepared from specimens on which ultrasonic attenuation measurements and measurements of corresponding weight loss are made over a period of time. An apparatus for making the ultrasonic attenuation measurements is shown in FIG. 1, and comprises an acoustic probe 10 adapted to transmit ultrasonic waves towards a composite article 20 to be checked and to receive ultrasonic signals reflected by the article 20. The probe 10 is connected to an electrical signal generator 30 adapted to output a repetitive electric signal pulse and to receive return electric signals from the probe. The signal trace transmitted by the probe 10 can be displayed on the screen of an oscilloscope 40 connected to the output of the signal generator 30. The probe 10, which is shown in longitudinal section in FIG. 1, comprises a transducer 11 for transmitting and receiving ultrasonic waves, the transducer 11 being embedded in a longitudinal recess in a cylindrical vessel 12 filled with water. The vessel 12 comprises a surface 13 which is remote from the transducer and is adapted to be placed in contact with the composite article 20 to be checked, the water 1 in the vessel 12 serving as a coupling fluid between the transducer 11 and the article 20. Since the propagation of ultrasonic waves in water has well-known characteristics, the use of water as a coupling fluid facilitates accurate measurement of ultrasonic wave attenuation in the composite material 20. The operation of this apparatus to measure ultrasonic wave attenuation in a composite material is as follows.

The acoustic probe 10 is applied to one surface of the composite material to be checked, after which a repetitive electrical signal pulse is produced by the signal generator 30 and applied to the input of the acoustic transducer 11. The transducer converts the electrical signal into ultrasonic waves by the piezoelectric effect and transmits these waves towards the article 20 to be checked. The transmitted ultrasonic waves are propagated in consecutive different media 1, 2, 3 and are partly reflected at the two interfaces encountered between the media 1, 2, 3. The first medium 1 is the water in the vessel, the second medium 2 is the composite material to be checked, and the third medium 3 can be water or air. The ultrasonic waves reflected at the two interfaces, namely the interface between the media 1 and 2 and the interface between the media 2 and 3, form two echoes. The two echoes are received by the acoustic transducer 11, which converts them back into electrical signals by the reverse piezoelectric effect. These electrical signals are output by the acoustic transducer 11 and displayed on the screen of the oscilloscope 40. The measurement of the amplitudes AO and A1 of the two electrical signals corresponding to the two echoes is then used to determined the ultrasonic wave attenuation in the composite material, as hereinafter described with reference to FIG. 2 which shows an example of the electrical signals displayed on the oscilloscope screen of the apparatus.

Figure 2:
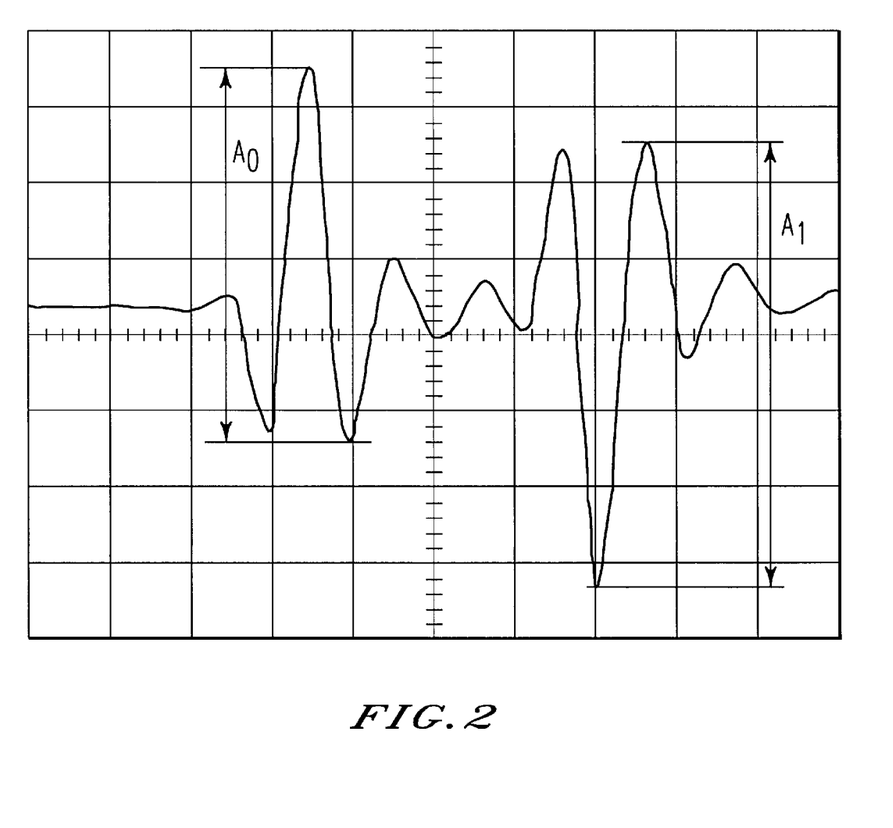
FIG. 2 is a diagram showing examples of electrical signals output by the measuring apparatus shown in FIG. 1.

The signals displayed correspond to the echoes associated with the reflections of the ultrasonic waves at the two interfaces between the water and the composite and between the composite and the medium 3, which may be either water or air. The first signal of amplitude AO corresponds to the reflection of the waves at the water/composite interface. The second signal of amplitude A1 is out of phase with the first signal and corresponds to the reflection of the wave at the second composite/medium 3 interface. For a composite material in the form of a plate of thickness d, the expression (in Neper/meter) of the ultrasonic wave attenuation α in the composite material is obtained by one of the following formulae (a) or (b) depending on whether the medium 3 is (a) water or (b) air.

$$\alpha = (1/2d) . L_N [(A0/A1) . (4Z_2 Z_3 / Z_2 + Z_3)^2] \quad (a)$$

$$\alpha = (1/2d) . L_N [(A0/A1) . (4Z_2 Z_3 / Z^2_2 - Z^2_3) ] \quad (b)$$

where $L_N$ is the Neper Logarithm and $Z_2$ and $Z_3$ are respectively the acoustic impedances of water and of the particular composite material concerned.

The acoustic impedance of a medium is defined as the product of the density of the medium by the speed of the ultrasonic waves being propagated therein. For instance, for water at ambient temperature:

$$Z_2 = 1.447 . 10^6 \, \Omega_{ac}.$$

The density of the composite material can be determined, for example, by double weighing (in air and in water). The speed of ultrasonic waves in the composite material can be determined by any known method.

Figure 3A:
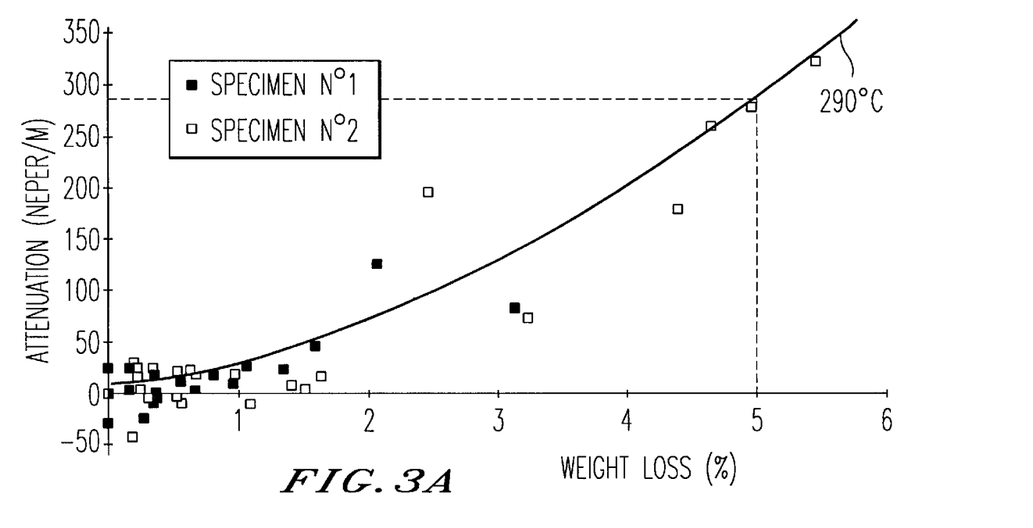
FIG. 3a shows a graph plotting the change of ultrasonic wave attenuation in a composite material PMR15 as a function of weight loss of the material at a reference temperature of 290° C.
Figure 3B:
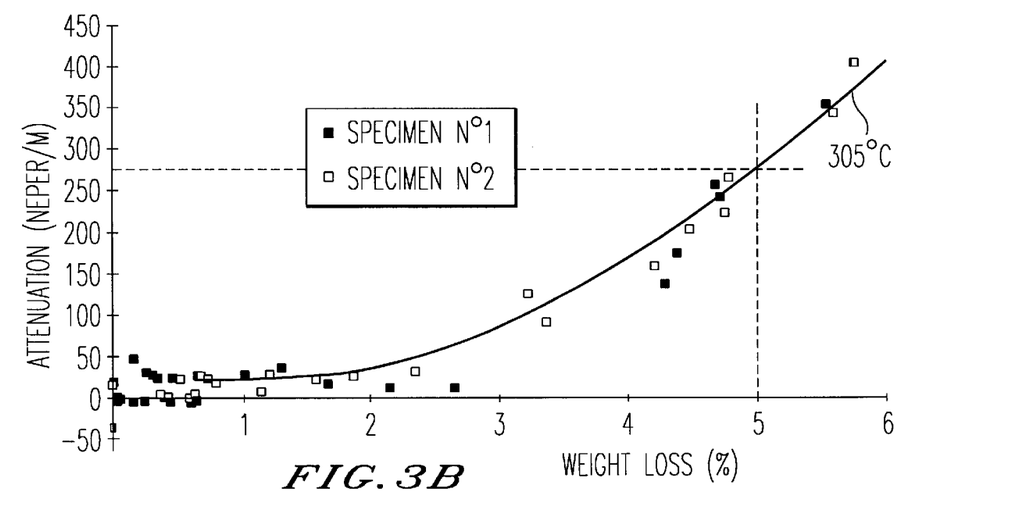
FIG. 3b shows a graph similar to that of FIG. 3a, but plotted for a reference temperature of 305° C.
Figure 3C:
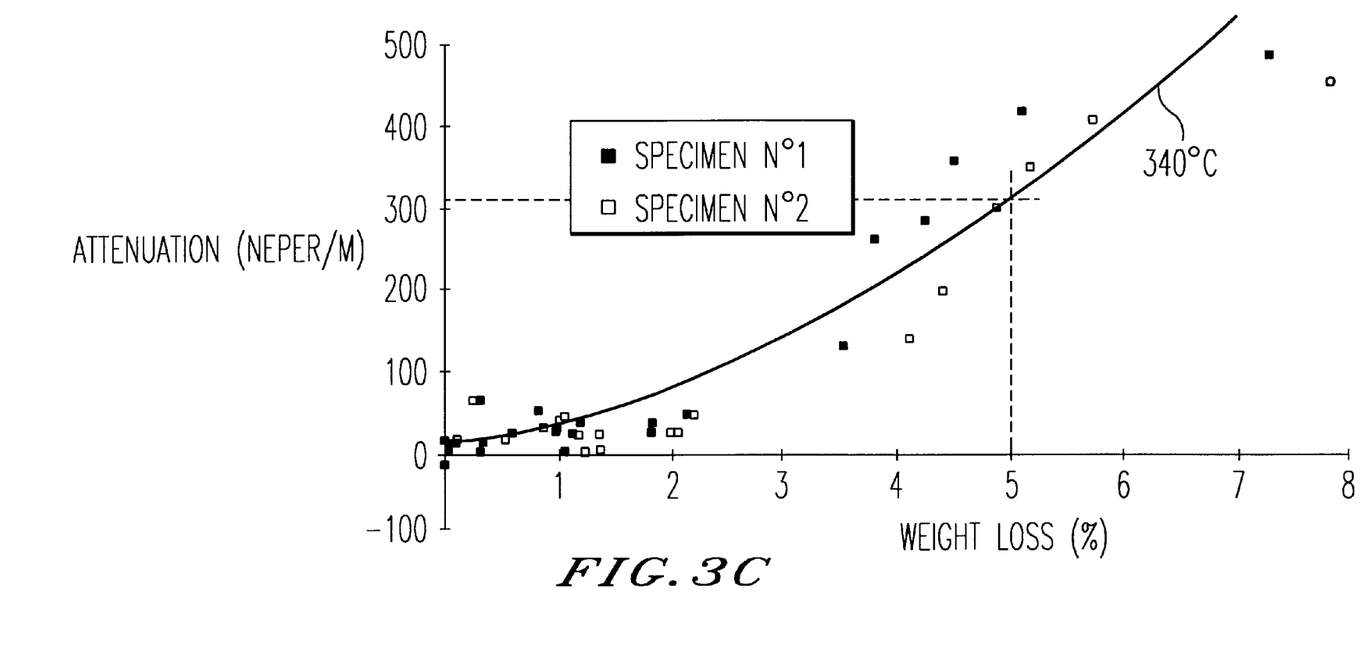
FIG. 3c shows a graph similar to that of FIG. 3a, but plotted for a reference temperature of 340° C.

FIGS. 3a, 3b and 3c show examples of graphs representing the change in ultrasonic wave attenuation in a composite material PMR15 as a function of weight loss at different temperatures.

Since the degradation of a composite material over time develops slowly, measurements of attenuation and weight loss are made by accelerating the ageing process of the composite material.

Accelerated ageing is achieved by heating the composite material to a temperature above its normal working temperature in order to speed up the degradation of the material and observe the effects in a reasonable time. However, it is important not to exceed a limit temperature beyond which some other degradation process of the composite material is observed, for it then becomes impossible to extrapolate the measurements to lower temperatures. This other degradation process may be due, for example, to a deterioration of the fibres which is superimposed upon the deterioration of the resin of the composite material. The limit temperature depends upon the particular composite material concerned and can be evaluated, for example, by making a prior thermodynamic study as described with reference to FIGS. 6 and 7 which show two graphs representing the variation in the life of two different composite materials as a function of the temperature to which they are subjected. In the case of the composite material known as PMR15 the limit temperature for accelerated ageing is 340° C.

In order to observe the influence of the ageing temperature on the change in attenuation as a function of weight loss, three graphs corresponding to three different ageing temperatures were prepared with the use of at least three specimens of the composite material PMR15. The three ageing temperatures chosen were 290° C. 305° C. and 340° C., and the three graphs are shown in FIGS. 3a, 3b and 3c.

Each graph is prepared as follows. A specimen of the composite material is placed in a stove and heated to a predetermined ageing temperature higher than the normal working temperature limit of the material. The specimen is removed from the stove after a predetermined time and ultrasonic wave attenuation in the specimen and the weight loss of the specimen are measured. To measure weight loss a balance accurate to one hundred thousandth of a gram is used in a climatised enclosure. The specimen is then replaced in the stove at the same ageing temperature for a predetermined time before being removed for further measurements of ultrasonic wave attenuation and weight loss. This sequence of operations is repeated a sufficient number of times to prepare a graph showing the change in ultrasonic wave attenuation plotted against weight loss of the composite material at the chosen isotherm. To refine the graph measurements can be made a number of times on a number of specimens. For example, two specimens were used in the preparation of each graph shown in FIGS. 3a, 3b and 3c. The three graphs obtained for three different ageing temperatures are similar if it is considered that the estimated attenuation value has a 10% uncertainty factor. The graphs therefore show that ultrasonic wave attenuation varies as a function of weight loss of the composite material irrespective of the ageing temperature applied thereto.

Consequently, the attenuation parameter can give an immediate idea of the thermal history of the composite material in terms of weight loss.

It is therefore sufficient to produce a single chart for a reference isotherm and for a given type of composite material in order to obtain an indicator of the extent of degradation of the composite material.

Figure 4:
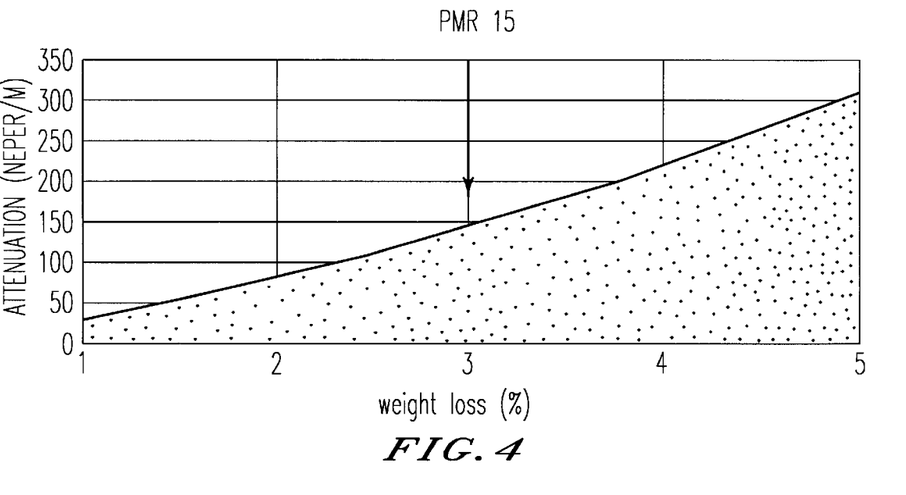
FIG. 4 shows an example of a chart produced in the preliminary phase of a method in accordance with the invention to characterise the change of weight loss of the composite material PMR15 as a function of ultrasonic wave attenuation in the material.
Figure 5:
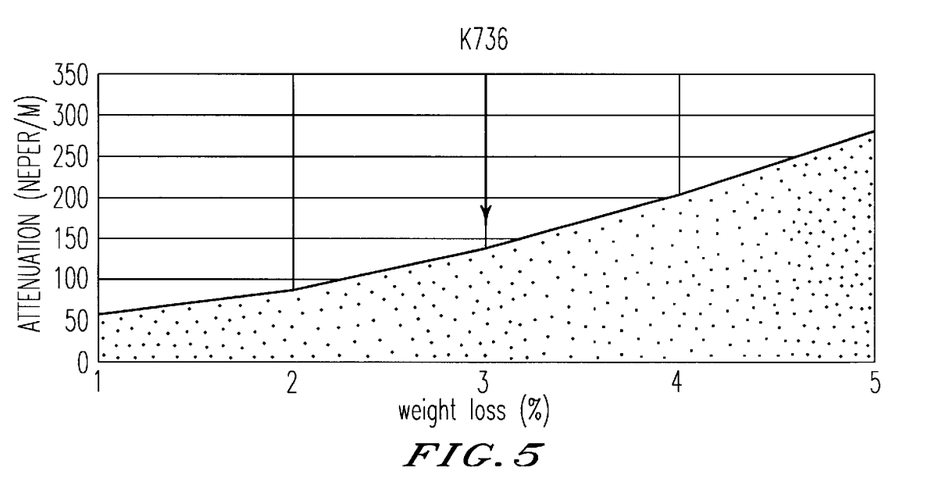
FIG. 5 shows an example of a chart similar to that of FIG. 4, but characterising the change of weight loss of the composite material known as Kerimid 736 as a function of ultrasonic wave attenuation in the material.

FIGS. 4 and 5 show two examples of charts made for two different composite materials known as PMR15 and Kerimid 736 respectively. The chart of FIG. 4 relates to PMR15 and was made at a reference temperature of 315° C., and the chart of FIG. 5 relates to Kerimid 736 and was made at a temperature of 220° C. The charts help to provide an indication of the ageing of the particular composite material concerned on the basis of just a single measurement of ultrasonic wave attenuation in the material. More particularly, the charts help to determine from a single attenuation measurement whether the use limit of the composite material in terms of weight loss has been reached. In the aviation field this use limit is set at a 3% weight loss relative to the initial weight of the composite material. The charts of FIGS. 4 and 5 show that this use limit corresponds to an ultrasonic wave attenuation of the order of 140 Nepers per meter for the two composite materials PMR15 and Kerimid 736.

These charts also show that in the initial stage before the application of the ageing process there is a residual ultrasonic wave attenuation in the composite material. The residual attenuation depends upon the porosity of the material and upon the proportions of the two phases, i.e. the fibres and the resin, which coexist in the material. The ageing effect is much greater than the residual attenuation. These charts therefore serve as tools for assessing the degradation of an article made of the particular composite material, and make it possible for an operator to follow the continuous change in the composite article non-destructively.

Figure 6:
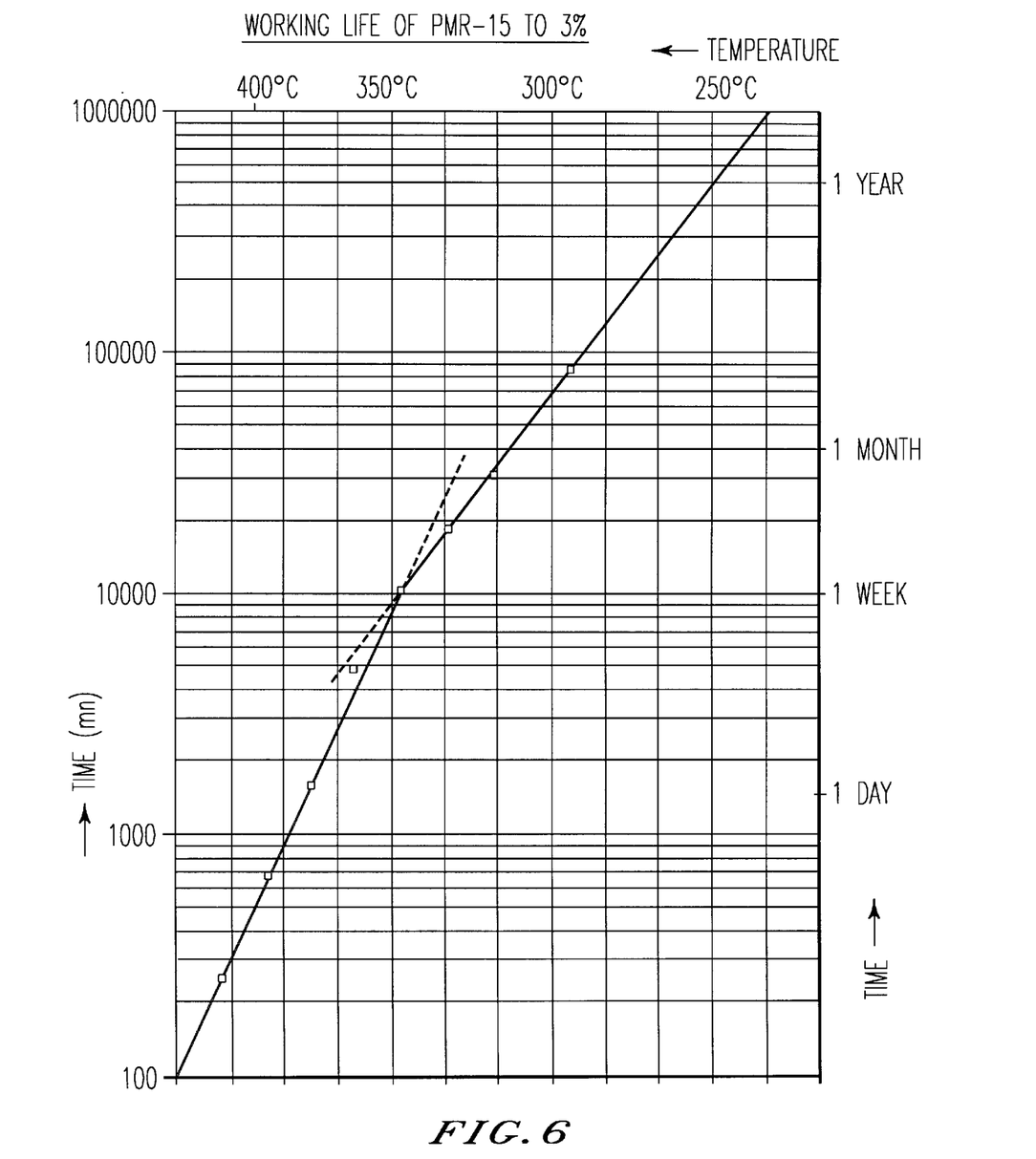
FIG. 6 shows a graph illustrating the change in the working life of the composite material PMR15 as a function of the temperature applied to the material.
Figure 7:
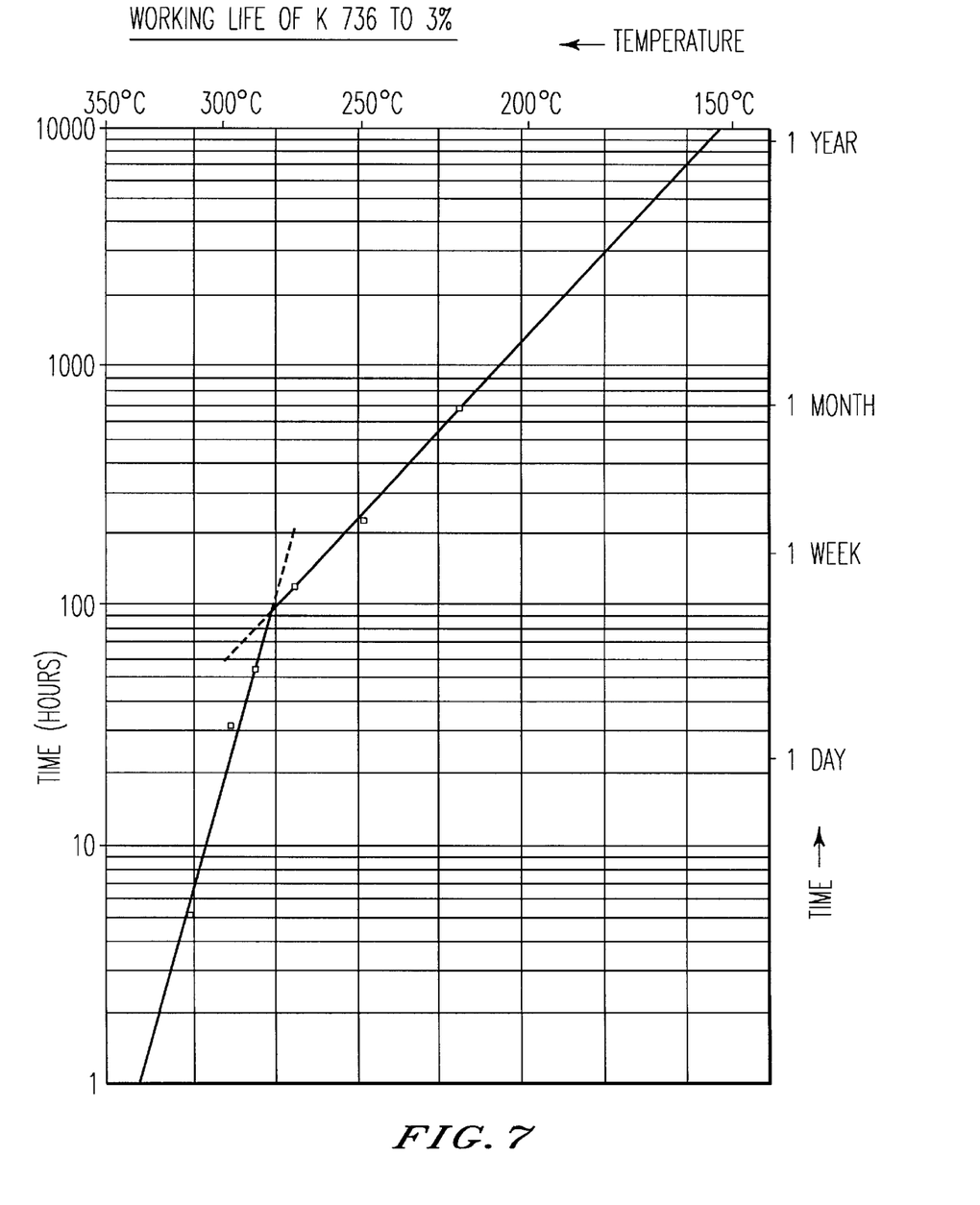
FIG. 7 shows a graph similar to that of FIG. 6, but illustrating the change in the working life of the composite material Kerimid 736 as a function of the temperature applied to the material.

FIGS. 6 and 7 show two graphs representing the change in the life of two different composite materials, PMR15 and Kerimid 736 respectively, as a function of the temperature applied to them. The graphs were obtained experimentally by fixing a 3% weight loss threshold of the material relative to its initial weight as the limit for the use of the material. Each measurement point is obtained by heating a specimen to a predetermined temperature in consecutive time intervals and measuring the weight loss of the specimen after each time interval, the operation continuing until the specimen weight loss is of the order of 3% and the time taken to reach this point being plotted on the graph. Different specimens are used for the different measurement points. A balance accurate to one hundred thousandth of a gram was used to measure the weight loss of the specimens. The graphs show that above an intrinsic temperature limit for a composite material, being of the order of 340° C. for a PMR15 composite and of the order of 280° C. for a Kerimid 736 composite, the material experiences an additional degradation process different from the ageing-associated process. Above this temperature limit the effects due to the two degradation processes are cumulative, leading to a much faster weight loss change than at lower temperatures. Consequently, if the charts of FIGS. 4 and 5 are to provide an indication of the ageing of a particular composite material based on only a single ultrasonic wave attenuation measurement, the charts must be produced at a reference temperature below the intrinsic temperature limit of the composite material.

When the chart characterising the change of weight loss of a given composite material as a function of ultrasonic wave attenuation therein has been prepared, the phase of checking articles made of the same composite material can be implemented. In this checking phase the apparatus described with reference to FIG. 1 is used to measure ultrasonic wave attenuation in the article, whereafter the chart prepared in the preliminary phase is used to deduce the corresponding weight loss and decide whether the article can be used further or needs replacing. This check is non-destructive and can be carried out at any time and as often as required.

The invention is not limited to the specific examples which have been described, and can be used for any kind of composite material.

We claim:

1. A non-destructive process for estimating the ageing of an article made of a composite material, comprising:
    a preliminary phase consisting of the step of preparing at least one chart characterising the change in the attenuation of ultrasonic waves in said composite material as a function of weight loss of said composite material; and
    a checking phase consisting of the steps of:
        measuring the attenuation of ultrasonic waves in said article, and
        determining the weight loss of said article using the chart prepared in said preliminary phase.

2. A process according to claim 1, wherein said chart is prepared by taking weight loss readings and ultrasonic attenuation measurements in specimens repeatedly over a period of time.

3. A process according to claim 1, wherein said chart is made for a given reference temperature.

4. A process according to claim 3, wherein the reference temperature is above the normal working temperature of the composite material article which is to be checked and below an intrinsic temperature limit for the composite material concerned.

* * * * *

UNITED STATES PATENT AND TRADEMARK OFFICE
CERTIFICATE OF CORRECTION

PATENT NO. : 5,922,957
DATED : JULY 13, 1999
INVENTOR(S) : Jean-Yves F.R. CHATELLIER, et al.

It is certified that error appears in the above-identified patent and that said Letters Patent is hereby corrected as shown below:

Column 4, line 23, after "290⁰ C.", please insert --,--;

line 40, after the word "graph", please insert --,--.

Signed and Sealed this

Twenty-sixth Day of September, 2000

Attest:

Q. TODD DICKINSON

*Attesting Officer*          *Director of Patents and Trademarks*